United States Patent

Pfleiderer et al.

[11] 4,060,239
[45] Nov. 29, 1977

[54] ERGOMETER WITH AUTOMATIC LOAD CONTROL SYSTEM

[75] Inventors: Werner Pfleiderer, Eningen; Friedrich Arnold, Reutlingen; Richard Häussermann, Pfullingen, all of Germany

[73] Assignee: Keiper Trainingsysteme GmbH & Co., Rockenhausen, Germany

[21] Appl. No.: 721,780

[22] Filed: Sept. 9, 1976

[30] Foreign Application Priority Data

Sept. 11, 1975 Germany .............................. 2540492

[51] Int. Cl.² .................... A61B 5/05; A63B 21/24
[52] U.S. Cl. ........................ 272/73; 272/DIG. 6; 73/379; 322/27; 272/129
[58] Field of Search ............ 272/73, DIG. 6, 129; 73/379; 322/27, 28, 29

[56] References Cited

U.S. PATENT DOCUMENTS

| | | | |
|---|---|---|---|
| 3,057,201 | 10/1962 | Jaeger | 272/DIG. 6 |
| 3,589,193 | 6/1971 | Thornton | 73/379 R |
| 3,765,245 | 10/1973 | Haupl | 73/379 |
| 3,845,756 | 11/1974 | Olsson | 128/2.06 R |
| 3,984,666 | 10/1976 | Barrou | 235/151.3 |

Primary Examiner—Robert W. Michell
Assistant Examiner—Francis J. Jaworski
Attorney, Agent, or Firm—Wigman & Cohen

[57] ABSTRACT

An ergometer including a generator, a cooling fan for the generator, and an electronic circuit control for compensating for the mechanical losses thereof whereby the electrical load of the generator can be maintained within pre-set values.

5 Claims, 3 Drawing Figures

U.S. Patent
Nov. 29, 1977
4,060,239
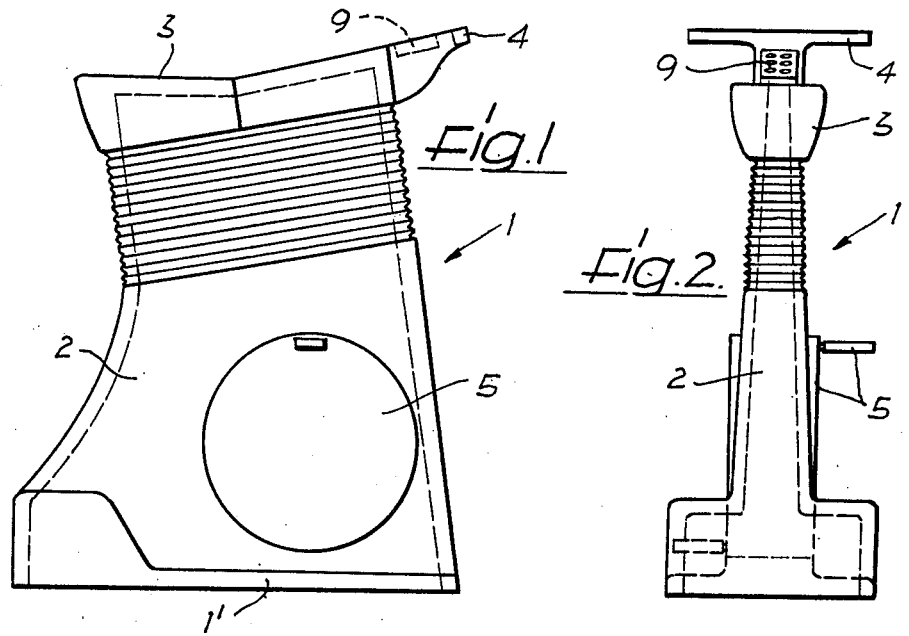
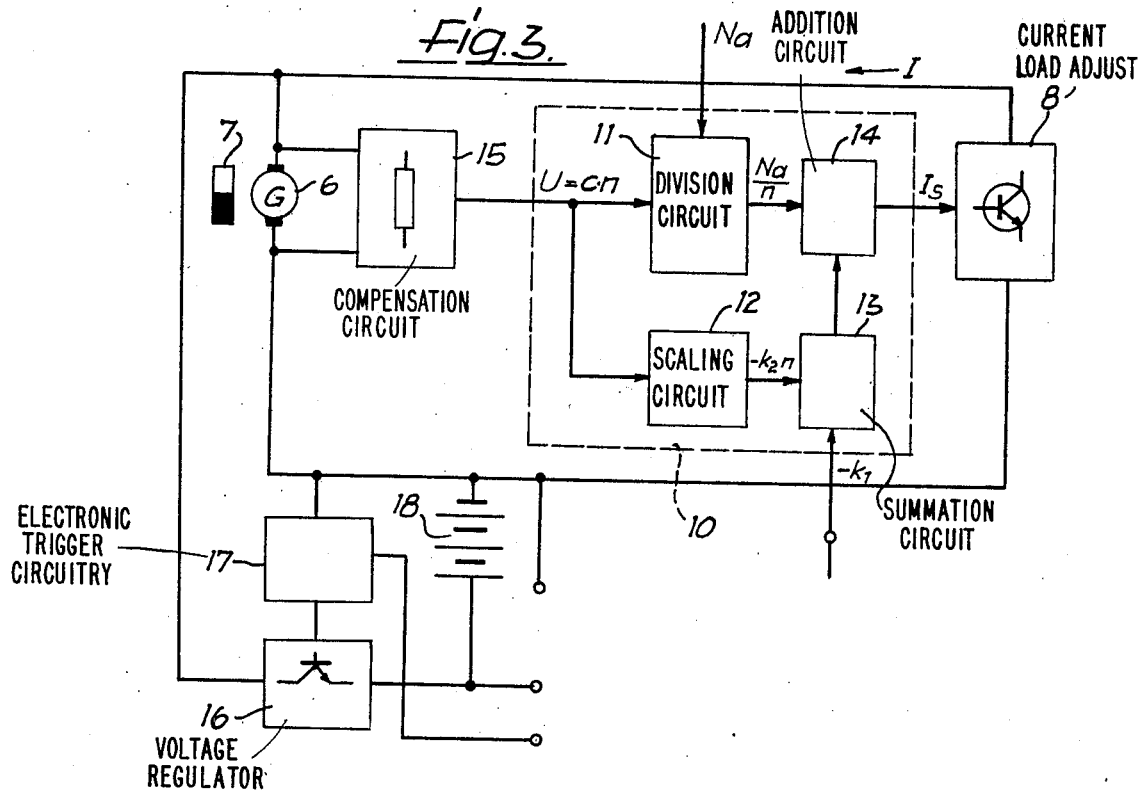

ERGOMETER WITH AUTOMATIC LOAD CONTROL SYSTEM

BACKGROUND OF THE INVENTION

This invention relates broadly to ergometers of the bicycle type for subjecting a patient being examined to physical stress.

More particularly, this invention relates to an erogmeter which includes a direct current generator which is operated by the patient being tested. Permanent magnets are provided to produce an exciter field. A loading device which is connected to the outlet of the generator includes an electronic load adjusting device for keeping the electrical load of the generator at the pre-set value. An electronic control is fed by the generator which determines the nominal value to be set in the loading device by taking into consideration the additional load caused by mechanical losses of the machine.

In the case of a known ergometer of this kind (German Pat. No. DT-OS 1,616,895), the nominal value is composed of a constant voltage produced with the help of a circuit connected to the generator and a voltage proportional to the speed of the generator which is produced by means of a tacho-machine. However, such a device is relatively expensive and suffers from the additional disadvantage that the output produced by the patient is not independent of the speed where the ergometer is provided with a fan for cooling the generator, the mechanical losses are related to the speed, i.e., a quadratic dependence. If no fan is provided, the generator must be of considerably larger design which contributes to the cost of the apparatus.

In view of the foregoing, it is apparent that there still exists a need for an ergometer which is not subject to the aforementioned disadvantages. It is therefore a primary object of this invention to provide an ergometer which is of relatively low cost and which can be operated in a manner so that the output is kept independent of the speed for all selected output values.

SUMMARY OF THE INVENTION

The present ergometer accomplishes the objectives, as aforementioned by including a control circuit having a nominal value dimension of the load current as a difference from a first portion, on the one hand, and the sum of the second and third portions, on the other hand. Thus, the first portion is proportional to the quotient of the output produced by the person being tested and the generator voltage; the second portion is proportional to the generator voltage; and the third portion is a constant.

The formation of the individual portions as well as the summation of the second and third portions and the difference formation are possible with simple electronic circuits. Furthermore, this nominal value formation takes into consideration the mechanical losses of the apparatus and is not linearly dependent on the speed as occurs with the fan. Therefore, with the present invention a fan can be provided which does not only represent an advantage in view of the admissible utilization of the generator but also for the heat elimination from the loading device and possibly also from the other electronic circuits.

In a preferred embodiment, the load adjusting device has a PI-control to which the nominal value dimension of the load current is supplied as control dimension. In this way the load current can be controlled in a sufficiently correct manner at comparatively low expense.

When the patient's output is to be selective within relatively wide limits, it is also necessary to be able to adjust the load current within correspondingly wide limits. As a rule the internal resistance of the generator is not small enough so as to be considered negligible and the output voltage of the generator will change depending on its speed as well as on the load current. In order to eliminate the error in the adjustment of the load current caused by the aforementioned circumstances, there is provided in the preferred embodiment means for compensating the internal resistance of the generator. The means for compensating is operatively connected to the generator which then supplies a voltage independent of the internal resistance of the generator, i.e., a voltage which depends only on speed.

It is also desirable to utilize for electrical as well as physiological reasons a minimum speed of the generator before the ergometer is completely ready for operation. A trigger circuit responding to a pre-set speed range is connected to the generator which functions to visually indicate whether the speed of the generator is within the pre-set speed range.

The generator is operatively connected to a voltage regulator for producing a constant output voltage. In this manner there is available a constant operating voltage for the energy supply to the electronic cirucits of the ergometer and also for charging a buffer battery.

With these and other objects, advantages and features of the invention, the nature of the invention will be more clearly understood by reference to the following detailed description of the invention, the appended claims and to the drawing.

BRIEF DESCRIPTION OF THE DRAWING

FIG. 1 is an elevational view of the ergometer according to the present invention;

FIG. 2 is an elevational front view of the ergometer according to the present invention; and FIG. 3 is a schematic diagram of the electrical circuitry employed in the ergometer of the present invention.

DETAILED DESCRIPTION OF A PREFERRED EMBODIMENT

Referring now to the drawing wherein like reference numerals are referred to in the several views shown in FIGS. 1 and 2 the reference numeral 1 refers to an ergometer made in accordance with the present invention.

Ergometer 1 has a casing 2 placed on a foundation plate 1'. At the upper side of ergometer 1, a seat 3 and a handle 4 are provided for the patient being tested. In the lower part of the casing 2 of foot pedal 5 is provided which is rotated by the patient with his feet. A direct current generator 6 (FIG. 3) is operatively connected with the foot pedal 5 over a drive (not shown) and which can be a V-belt drive. Permanent magnets 7 are provided for the production of the exciter field. A fan, (not shown) is also operatively connected to the foot pedal 5 with suitable drive means for cooling the generator 6.

A load adjusting device 8 connected to the output terminals of the generator 6 contains electronic elements for adjusting the load current I at different values. In order to keep the load current at a pre-set nominal value and to change the load current to correspond with the modification of the nominal value, the load adjusting device 8 contains a PI-regulator (not shown).

For the output $N_a$ to be supplied at the foot pedal 5, the following equation is applicable:

$$N_a = N_{el} + N_R + N_L$$

whereby $N_{el}$ represents the electrical output of the generator 6 supplied to the load adjusting device 8;

$N_R$ represents the friction power occuring, for example, in the foot pedal 5, in the drive between it and the generator 6 as well as within the latter; and $N_L$ represents the drive power for the fan.

since the friction power is proportional to the speed and the fan output is approximately proportional to the square of the speed, the equation $$N_a = U \cdot I + k_1 \cdot n + k_2 \cdot n^2 \qquad (2)$$

is obtained for the output to be produced at the foot pedal, whereby $U$ is the generator voltage;
$I$ is the load current;
$n$ is the speed; and
$k_1$ and $k_2$ are to constants.

Owing to the excitation of the generator 6 by means of permanent magnets 7 the generator voltage is shown as $$U = c \cdot n \qquad (3)$$

whereby $c$ is a constant.

When $U$ is placed into equation (2) the load current $I$ can be determined, as follows:

$$I = 1/c \, ( \, (N_a/n) - (k_1 + k_2 \cdot n) \, ) \qquad (4)$$

The output $N_a$ to be produced at the foot pedal 5 is fed to control circuit 10 in a binary manner over a keyboard 9 (FIG. 1) arranged at the upper side of the casing 2 and which forms the control dimension for the PI-control of the load adjusting device 8 corresponding to the nominal value $I_s$ of the load current. As shown in FIG. 3, the dimension $N_a$ is supplied to an electronic division circuit 11 which also receives the dimension $U = c \cdot n$. From these two values, the division circuit 11 froms the quotient $N_a/n$ as first portion of the dimension of the dimension of the nominal value. The generator voltage $U = c \cdot n$ is supplied to an additional electronic circuit 12 which, on the basis of this dimension, forms the portion $k_2 \cdot n$ of the nominal value. This portion is added to a portion $k_1$ in a summation circuit 13. An addition circuit 14 forms the difference between the value $N_a/n$ and the sum $k_1 = k_2 \cdot n$. This difference is supplied to the PI-control of the load adjusting device 8 as control dimension. The load adjusting device 8 thus maintains the ouput $N_a$ to be produced at the foot pedal 5 at the pre-set nominal value independently of the speed of the generator 6.

Due to the internal resistance of the generator 6, its output voltage is not only dependent on the speed but also on the load. This dependence on the load is not taken into considertion when forming the nominal value. A compensation circuit 15 is connected to the genertor 6 which supplied the voltage U, which is only dependent on the speed, to the control circuit 10.

Voltage regulator 16 as well as electronic trigger circuit 17 are also connected to the generator 6. Voltage regulator 16 produces, on the basis of the generator voltage, a constant supply voltage for the electronic device of ergometer 1 and the charging of buffer battery 18. The trigger 17 responds when the speed of the generator 6 is within a preset range. This signal can, for example, be used to control a signal lamp. Such a speed control is useful since, below a minimum speed, the generator 6 does not produce the required minimum voltage.

Although only a preferred embodiment of the ergometer of this invention is specifically illustrated and described herein, it will be understood that many variations and modifications of the present invention are possible in light of the above teachings and within the purview of the appended claims without departing from the spirit and intended scope of the invention.

What is claimed:

1. An ergometer comprising a direct current generator which is operatively connected with a driving device to be operated by the person being tested, permanent magnets for producing an exciter field, a loading device connected to the outlet of the generator with an electronic load adjusting device for keeping the electrical load of the generator at the pre-set value and an electronic control circuit fed by the generator which determines the nominal value to be set in the loading device, the nominal value being a function of the additional load caused by mechanical losses, wherein the improvement comprises an electronic control circuit including means for providing a nominal value dimension of the load current as a difference from a first portion, on the one hand, and the sum of the second and third portions, on the other hand, whereby the first share is proportional to the quotient of the output ($N_a$) to the produced by the person being tested and the generator voltage (U), the second share being proportional to the generator voltage (U) and the third portion being constant.

2. An ergometer according to claim 1, wherein the load adjusting device comprises a PI-control to which the nominal value dimension of the load current is supplied as the control dimension.

3. An ergometer according to claim 1 further including a compensator to compensate for the internal resistance in the generator, said compensator being connected in parallel to the generator.

4. An ergometer according to claim 1 further including a trigger circuit means operatively connected to the generator for responding within a pre-set range of speed.

5. An ergometer according to claim 1 further including a voltage regulator means operatively connected to the generator for producing a constant output voltage.

* * * * *